United States Patent [19]

Haase

[11] Patent Number: 4,710,757

[45] Date of Patent: Dec. 1, 1987

[54] PLANTER MONITOR SYSTEM

[76] Inventor: Wayne C. Haase, 2764 Doverton Sq., Mountain View, Calif. 94040

[21] Appl. No.: 580,108

[22] Filed: Feb. 14, 1984

[51] Int. Cl.$^4$ ............................................. G08B 21/00
[52] U.S. Cl. ................................. 340/684; 324/61 R; 111/1
[58] Field of Search ............... 340/684, 674, 562, 606, 340/609, ; 111/1; 221/3, 7, 8; 324/61.1 R, 71.4; 377/6, 10–12; 73/861.08; 361/280

[56] References Cited

U.S. PATENT DOCUMENTS

| | | | |
|---|---|---|---|
| 3,450,988 | 6/1969 | Breen et al. | 324/61 R |
| 3,469,157 | 11/1969 | Rhodes | 111/1 X |
| 3,515,884 | 6/1970 | Imadate | 377/12 |
| 3,551,919 | 1/1971 | Forbes | 340/562 |
| 3,641,543 | 2/1972 | Rigby | 340/609 |
| 3,754,172 | 8/1973 | Hoffmann | 361/280 |
| 3,824,460 | 6/1974 | Gustafson | 340/562 X |
| 4,004,289 | 1/1977 | Kirk | 340/684 X |
| 4,079,362 | 3/1978 | Grimm et al. | 340/684 |
| 4,223,751 | 9/1980 | Ayers et al. | 177/50 |
| 4,258,326 | 3/1981 | Johne | 340/562 X |
| 4,320,766 | 3/1982 | Alihanka et al. | 340/562 |
| 4,333,096 | 6/1982 | Jenkins et al. | 340/684 |

Primary Examiner—James L. Rowland
Assistant Examiner—Jeffery A. Hofsass
Attorney, Agent, or Firm—James F. Mitchell

[57] ABSTRACT

This invention monitors the presence of or a flow of discrete small particles having a high dielectric constant, particularly seeds being planted by a seed planting machine. The invention uses the high dielectric constant of the particles, such as seeds, passing at least a pair of spaced electrodes to vary the capacitance between them and thereby indicate presence of the seed. The capacitance variation is detected and then processed by console located display, alarm and/or counting circuitry.

12 Claims, 9 Drawing Figures

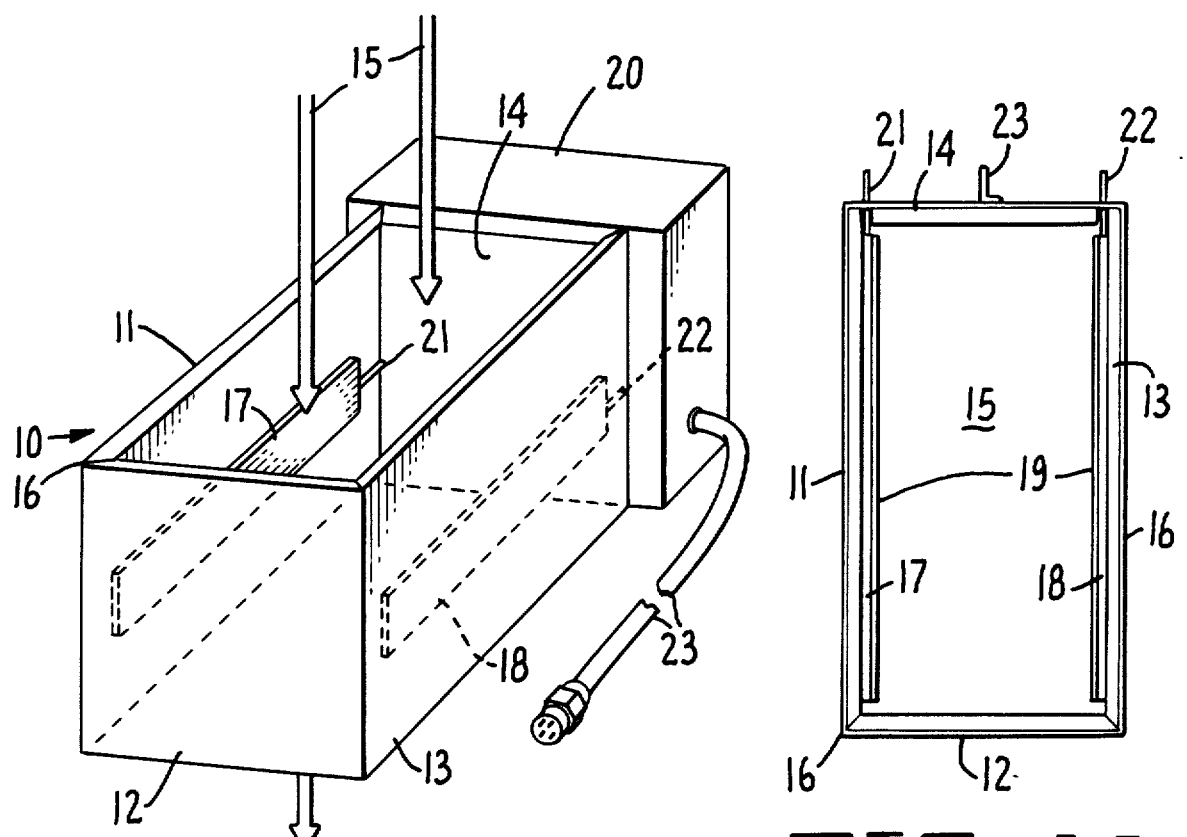
FIG. 1.
FIG. 1A.
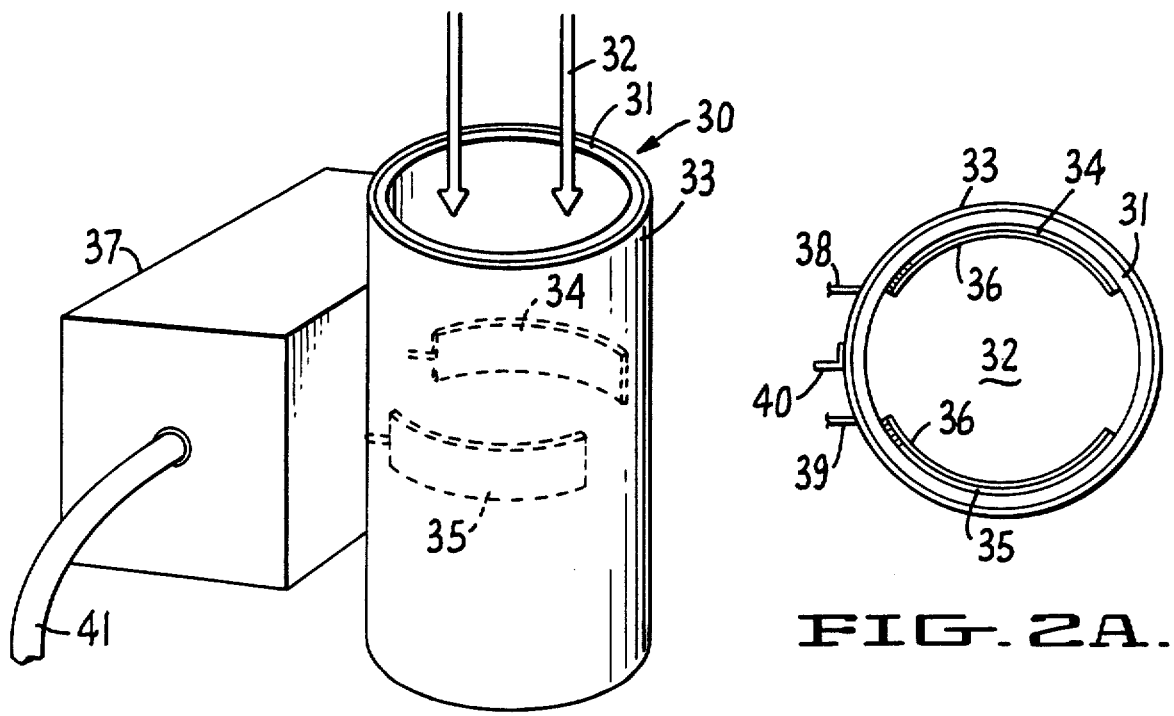
FIG. 2.
FIG. 2A.

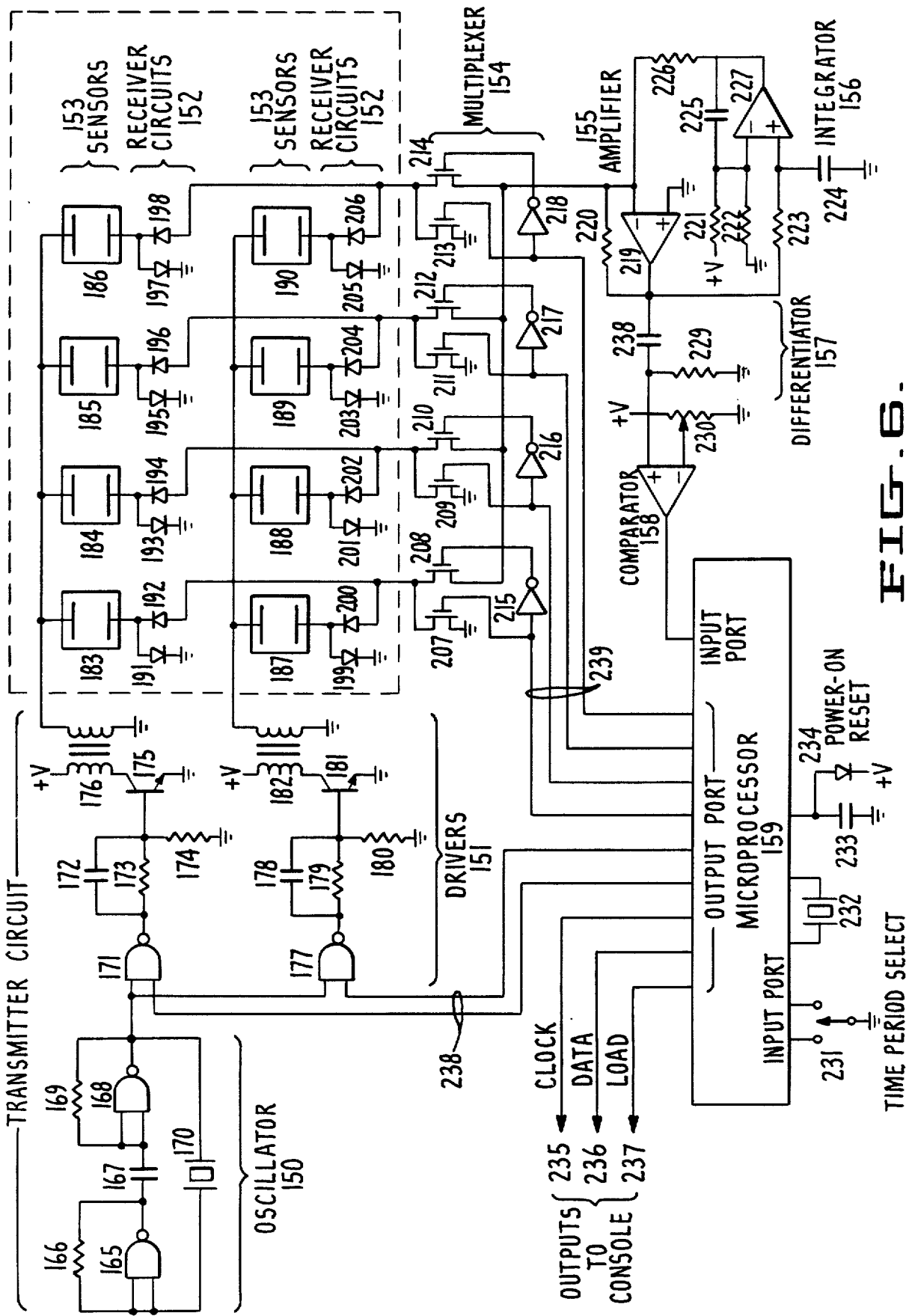

PLANTER MONITOR SYSTEM

BACKGROUND OF THE INVENTION

Seed planters usually include a plurality of seed feeding devices, one for each row being planted. The devices usually include a housing or other means forming a path of travel for seeds to transverse on their way to the ground to be planted. Several types of seed planter monitors utilizing different types of seed sensors in the seed path have been used in the past. One type of seed sensor incorporates mechanical switches which are actuated as a result of physical contact with the seeds, an example of which is described in U.S. Pat. No. 3,632,918. Photoelectric or optical seed sensors which operate by the blocking of a light beam from a light source to a photodetector by the seed have also been used, an example of which is described in U.S. Pat. No. 4,166,948.

In order to have sufficient sensitivity for grain detection, mechanical seed sensors must be designed in such a manner that they are easily deflected by small forces. Consequently, they are sensitive to planter vibration, a problem that is particularly acute for small seeds such as what as wheat or vegetables. Furthermore, the mechanical sensors are designed to have an element interposed in the actual seed path and can consequently block all or part of the seed flow if worn or damaged.

The photoelectric or optical seed sensors are typically designed to operate in a narrowing or constriction of the seed path in order to insure that an individual seed is able to block the light path. This constriction, which "focusses" the seed flow, is subject to blockage by oversize seeds or foreign material, a problem especially important for planters that plant the smaller seeds such as wheat or vegetables. Photoelectric sensors are generally sensitive to sunlight and must be designed to minimize light leakage from the external environment to the photodetector. In addition, photoelectric sensors are prone to reduced sensitivity by the gradual build-up of dust, dirt or deposit from various seed coatings or insecticide or fertilizer on both the light source and the photodetector.

Furthermore, it has heretofore been difficult or impossible to provide a single sensor apparatus capable of detecting different types or sizes of seeds. When the planter machine is changed from one type of seed to another, at least three problems are encountered. First, the difference in seed sizes presents a problem in that a given sensing arrangement having a fixed sensitivity for the purpose of detecting a large seed may fail to respond reliably to a substantially smaller seed. Second, the rate of planting may differ substantially for different typs of seeds such that a sensor having sufficient sensitivity for a relatively slow rate of planting may fail to respond rapidly enough to count all of the seeds being planted at a substantially higher planting rate. Third, the attitude or orientation of the seed may vary substantially when different types of seeds are planted or when different planting rates are used; this is particularly true for asymmetric seeds such as corn, wheat or lettuce.

In the foregoing seed planter monitors, a plurality of indicators are usually provided in the form of lamps corresponding to each seed sensor which flash each time a seed is sensed. This means that the operator must continuously watch the lamps to see whether seeds are being planted. Such arrangements are inconvenient to monitor especially when a large number of rows of seeds are being planted simultaneously since the operator must, among his other functions, continuously watch all the lamps to make sure they are flashing. Furthermore, in case of a malfunction of a single row, if the operator stops the planter, all rows stop planting operation and all lamps will cease to indicate which row was the source of the initial failure; the operator must then either check the planting devices for all the rows or else remember which row was the source of the failure. The task becomes increasingly more difficult as the number of planting rows is increased, for example in the case of wheat planters.

SUMMARY OF THE INVENTION

This invention monitors the presence of or a flow of discrete small particles having a high dielectric constant, particularly seeds being planted by a seed planting machine. The invention uses the high dielectric constant of the seeds passing at least a pair of spaced electrodes to vary the capacitance between them and thereby indicate presence of the seed. The capacitance variation is detected and then processed by console located display, alarm and/or counting circuitry.

A planter monitor system according to one form of the invention comprises a plurality of sensors for detecting the respective presence or flow of seeds through a plurality of seed paths, a console positioned on the tractor or vehicle in full view of the operator, and electrical cabling to interconnect the plurality of sensors to the console.

Each sensor comprises transmitter electrode means electrically exposed to the seed path for receiving electrical exposed to the seed path for receiving electrical energy from the transmitter electrode means, shielding means for electrically isolating the transmitter and the receiver electrode means from the external environment, transmitter circuit means for driving the transmitter electrode means with appropriate electrical signal to produce electrical energy, and receiver circuit means for deriving from the receiver electrode an electrical signal responsive to the electrical energy from the transmitter electrode means which may vary in response to momentary change in the electrical capacitance between the transmitter and receiver electrode means due to passage of a seed through the seed path in proximity to the electrode means.

The console comprises electrical circuits responsive to the electrical signals cabled to it directly from the sensor means, failure indicator lamp means to indicate to the operator which, if any, of the sensor fails to detect seed flow during a specified period of time and to continue to indicate the first failure detected by that sensor in the event of more than one failure detected by the sensors, proper-operation indicator lamp means to indicate to the operator proper planting operation of the planting machine if all of the sensors detect seed flow during the specified period of time to thereby give positive indication of proper operation of the planting machine and thereby eliminate ambiguity in the interpretation of the planting machine status in the event that one or more of the failure indicator lamp means had burned out, an audible alarm means to signal to the operator that a malfunction exists in the planting machine should he not be viewing the console in the event that one or more of said failure indicator lamp means is energized, and an adjustment means for establishing the value of the specified period of time.

In accordance with another aspect of the invention, the planter monitor system comprises a plurality of sensors for detecting the respective presence or flow of seeds through a plurality of seed paths, one or more detection circuit means for monitoring the electrical signals from more than one of the sensors, a console positioned on the tractor or vehicle in full view of the operator, and electrical cabling means to interconnect the plurality of sensors and the one or more detection circuit means to the console.

The sensors comprise transmitter electrode means electrically exposed to each seed path, receiver electrode means electrically exposed to each seed path for receiving electrical energy from the corresponding transmitter electrode means, shielding means for electrically isolating the transmitter electrode means and the receiver electrode means from the external environment, and receiver circuit means for deriving from the receiver electrode means a buffered electrical signal responsive to the electrical energy from the corresponding transmitter electrode means which may vary in response to momentary change in the electrical capacitance between transmitter and receiver electrode means due to passage of a seed through the seed path in proximity to that transmitter and receiver electrode means.

The console in this variation comprises electrical circuit means responsive to the output electrical signal from one or more detection circuit means as well as failure indicator lamp means, proper-operation indicator lamp means and an audible alarm means.

Accordingly, it is a general object of this invention to provide a monitor system with a new and improved sensor apparatus for accurately and reliably sensing the passage of discrete particles along a given path of travel.

A more specific object of the invention is to provide a monitor system with a new and improved sensor which is especially adapted for detecting the passage of seeds through a planting chute of a seed planting machine.

Another object of this invention is to provide a monitor system with a new and improved seed sensor which is insensitive to vibration in the planting machine.

Another object of this invention is to provide a monitor system with a new and improved seed sensor which is insensitive to the effects of sunlight.

Another object of this invention is to provide a monitor system with a new and improved seed sensor which is insensitive to the buildup of dust, dirt or deposit from various seed coatings.

Another object of this invention is to provide a monitor system with a new and improved seed sensor which is capable of detecting the passage of seeds through an opening of relatively large cross sectional area, which does not constrict, "focus" or otherwise interfere with the actual flow path of the seeds, and which can be fabricated in such a manner as to conform to the actual shape of the seed path.

Yet another object of this invention is to provide a monitor system with a new and improved seed sensor which is capable of detecting a wide range of seed types and sizes over a wide range of seed planting rates.

Another object of this invention is to provide a monitor system with a new and improved seed sensor which is suitable for monitoring a large number of planting rows.

Another object of this invention is to provide a monitor system with a new and improved sensor apparatus for accurately and reliably sensing the passage of fertilizer or herbicide pellets through a planting chute of a seed planting machine.

Still another object of this invention is to provide a monitor system which has an improved indicator apparatus which is easy to read and whereby an operator may readily and unambiguously ascertain the status of the planting machine.

Yet another object of this invention is to provide a monitor system which continues to indicate the source of an initial failure even after the planting machine is stopped and all planting operation ceases.

BRIEF DESCRIPTION OF THE DRAWINGS

FIG. 1 is a perspective view of a sensor designed for a seed path of rectangular cross section;

FIG. 1A is a vertical cross-sectional view of the sensor of FIG. 1;

FIG. 2 is a perspective view of a sensor designed for a seed path of circular cross section;

FIG. 2A is a horizontal sectional view of the sensor of FIG. 2;

FIG. 6 is an electrical schematic diagram of the sensors and detector circuit for an eight-row planter monitor system in accordance with another form of the invention.

DETAILED DESCRIPTION OF THE ILLUSTRATED EMBODIMENTS

Figure 3:
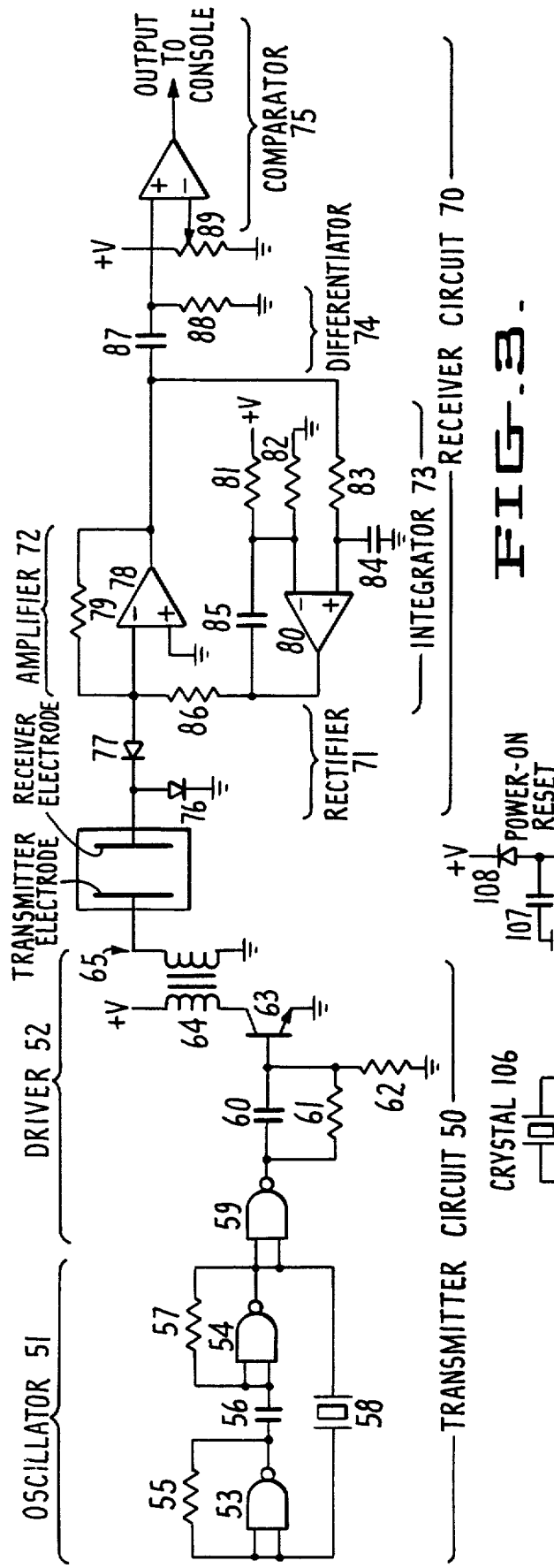
FIG. 3 is an electrical schematic diagram of the sensor electronics in accordance with one form of the invention.

Referring now to FIG. 1, a sensor is illustrated for use in a seed path of rectangular cross section. The sensor structure generally designated 10 is constructed of four sides 11,12,13,14 each fabricated from an insulating material such as plastic or epoxy-glass, and arranged to form part of the seed path 15 generally defined as the region between the four sides. The outside surface of the four sides is covered with a conductive shield 16 made from a material such as copper or brass which may be attached by adhesives or else deposited directly on the surface. This conductive shield 16 shields the structure from interference with external electrical signals and confines internal electrical fields.

On the inner surface of one side 11 is attached a transmitter electrode means 17, having a length slightly less than the length of the side 11 and a height considerably smaller than the height of side 11. The electrode means 17 is made from conductive material, such as copper or brass, and is attached either by adhesives or deposition. On the inner surface of the side 13 directly opposite side 11 is attached a receiver electrode means 18 similar to the transmitter electrode means 17. Both the receiver and the transmitter electrode means 17 and 18 are mounted approximately half way between the top and bottom edges of the sensor structure. The electrodes 17 and 18 may be covered by an additional insulating layer 19, which may be made from such materials as plastic or adhesive-backed mylar or the insulating layer 19 may be deposited directly as a coating. While not necessary for proper operation of the sensor, the insulating layer 19 prevents corrosion of the electrode means 17 and 18 and eliminates any potential harmful effects due to moisture in the seed path 15.

The transmitter electrode means 17 is connected electrically to a transmitter circuit means located in enclosure 20 attached to one side of the sensor structure by means of a wire 21. Similarly, the receiver electrode means 18 is connected electrically to a receiver circuit means also located in enclosure 20 by means of a wire 22. An additional wire 23 is attached to the conductive shield 16 and provides a ground connection to the circuits inside enclosure 20. The circuits in enclosure 20 are electrically connected to additional circuits, described later, through cable 23.

While FIGS. 1 and 1A show a structure of rectangular cross section, other shapes, such as trapezoidal and hexagonal, may be constructed in a manner similar to that described above.

Referring to FIG. 2, a sensor is illustrated for use in a seed path of circular cross section. The sensor structure generally designated 30 is constructed from a cylinder 31 made from an insulating material such as plastic. The region inside the structure defines the seed path 32. The outer surface of the cylinder 31 is covered with a conductive shield 33 made from a material such as copper or brass which may be attached by adhesives or else deposited directly on the surface. This conductive shield 33 shields the structure from interference with external electrical signals and confines internal electrical fields.

On the inner surface of the cylinder 31 is attached a transmitter electrode means 34 having a length approximately one-fourth of the inner circumference of the cylinder 31 and a height considerably less than the height of the cylinder 31. The electrode is made from conductive material, such as copper or brass, and is attached either by adhesives or deposition. A receiver electrode means 35, similar in shape to the transmitter electrode means 34, is also attached to the inner surface of the cylinder 31 at a point directly opposite the transmitter electrode means 34. Both the receiver and the transmitter electrode means 34,35 are mounted approximately half way between the top and the bottom of the cylinder 31. The electrode means 34,35 may be covered by an additional insulating layer 36, which may be made from such materials as plastic or adhesive-backed mylar or may be a deposited coating. While not necessary for proper operation of the sensor, the insulating layer 36 prevents corrosion of the electrode means 34,35 and eliminates any potential harmful effects due to moisture in the seed path 32.

The transmitter electrode means 34 is connected electrically to a transmitter circuit located in enclosure 37 attached to the cylinder 31 by means of a wire 38. Similarly, the receiver electrode means 35 is connected to a receiver circuit also located in enclosure 37 by means of a wire 39. An additional wire 40 is attached to shield 33 and provides a ground connection to the circuits inside the enclosure 37. The circuits in enclosure 37 are electrically connected to additional circuits, described later, through cable 41.

While FIGS. 2 and 2A show a structure of circular cross section, other shapes, such as elliptical, may be constructed in a manner similar to that described above.

By way of example, electrode means 34,35 for a cylinder 31 that is one inch in diameter and three inches long may be about 3/10 inch high and each extend about 90° on the inside cylinder wall. Electrode means 17,18 in the rectangular sensor of FIG. 1 may be about 0.15 inch high and 2 inches long with an electrode spacing of about ⅛ inch. The interelectrode capacitance is in the range of $1 \times 10-14$ to $10-15$ farads. The change in capacitance due to a passing seed is in the range of $1 \times 10-15$ to $10-17$ farads.

FIG. 3 shows the sensor electronics in accordance with one form of the invention using radio frequencies applied to the transmitter electrode means. The sensor electronics consist of a transmitter circuit means. The sensor electronics consist of circuit means 70. The transmitter circuit means 50 and receiver circuit means 70 are general purpose in the sense that they are able to operate with a variety of sensors, such as those described in FIGS. 1 and 2.

The transmitter circuit means 50 is comprised of an oscilator 51 and a driver circuit 52. The output of the driver circuit 65 is fed via wire (21 in FIG. 1 or 38 in FIG. 2) to the transmitter electrode means for the particular sensor.

The oscillator 51, formed by digital gates 53 and 54, resistors 55 and 57, capacitor 56 and crystal 58, generates a signal of constant frequency which is applied to the input of the driver circuit at gate 59. The driver circuit is comprised of buffer gate 59, capacitor 60, resistors 61 and 62, transistor 63, and transformer 64. The output of transformer 64 is a sinusoidal signal at a frequency equal to that of crystal 58, for example, at 5 MHz, and of sufficient amplitude in the order of 50 V to drive the transmitter electrode means for seed detection.

The receiver circuit means 70 is comprised of rectifier 71, amplifier 72, integrator 73, differentiator 74 and comparator 75. The input to the receiver circuit means 70 at rectifier 71 is connected to the receiver electrode means of the particular sensor (18 in FIG. 1 or 35 in FIG. 2).

The rectifier, formed by diodes 76 and 77, half-wave rectifies the current which passes through the sensor due to the electrical impedance between the transmitter and receiver electrode means. In the particular embodiment illustrated, the sensor current is primarily capacitive displacement current and consequently depends on the dielectric constant of the region between the two electrodes. Since the region between the two electrodes is a portion of the seed path, any change in the dielectric constant due to presence or motion of seeds between the electrodes will result in a change in the amplitude of the rectified current in diode 77. The dielectric constant of an individual seed is in the range of thirty to eighty times larger than that of air and so the sensor becomes particularly sensitive to the presence of seeds. However, since the dielectric constant of plastics and other materials from which the sensor structure is made lies in the range of only two to three times that of air, very little shunting of the electric field between the two electrodes occurs. As a result, relatively large changes in current occur in diode 77 as a result of the passage of only a single seed between the transmitter and receiver electrodes.

Amplifier 72, comprised of op amplifier 78 and resistor 79, converts the half-wave rectified current in diode 77 to a voltage the amplitude of which depends on the dielectric constant between the sensor electrode means.

Integrator 73, comprised of op amplifier 80, resistors 81, 82 and 83, and capacitors 84 and 85, acts as a d-c restoring circuit by injecting a current through resistor 86 back to amplifier 72 so as to keep the output voltage of amplifier 72 at a nominal value depending on the values of resistors 81 and 82. The inclusion of integrator 73 extends the dynamic range of the receiver circuit and allows the sensor to operate over a wide variation in capacitance between the sensor electrode means. Furthermore, integrator 73 allows the sensor to operate even if the space between the electrodes is virtually packed with dust, a condition which might otherwise cause the amplifier 72 to saturate.

Differentiator 74, comprised of capacitor 87 and resistor 88, generates an input signal to the positive input of comparator 75 which is dependent on the time rate of impedance between the sensor electrode means. That in turn is dependent on the passage of seeds between the electrodes. Comparator 75 compares the input signal to a fixed value, selectable by the setting of potentiometer 89, and produces a digital output equal to a logical ONE if the input exceeds the fixed value established by 89 whenever a seed passes between the sensor electrode means. Thus, the setting of potentiometer 89 in effect establishes the sensitivity of the receiver circuit and allows the receiver to be optimized for a particular range of seed sizes. The output of comparator 75 for each sensor in a multi-sensor system is then connected electrically to the console (described later) by means of a cable (not shown).

Figure 4:
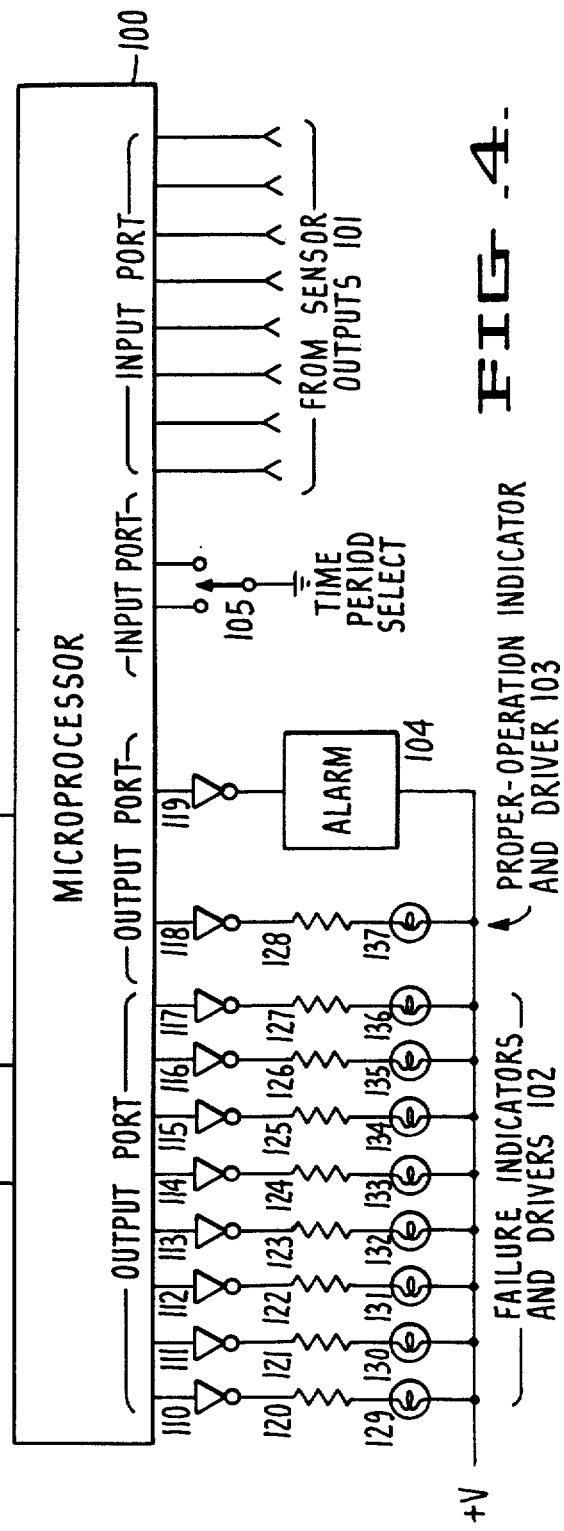
FIG. 4 is an electrical schematic diagram of the console electronics to be used with the circuits of FIG. 3.

FIG. 4 is an electrical schematic diagram for the console electronics for a multi-row planter monitor system. In the example shown, an eight row planter is assumed, although the method can be easily modified for either a larger or a smaller number of rows. In the particular example, eight sensors, as previously described, provide outputs which serve as inputs to the console electronics and are generally denoted 101. Corresponding to each input to the console electronics is an associated failure indicator and driver, generally denoted by 102. In addition to the failure indicators is a positive-operation indicator with driver the purpose of which is to give positive indication of proper planter functioning, and is designated 103. Furthermore, an audible alarm 104 with driver serves to attract the attention of the operator in the event that a row failure occurs while the operator is not watching the console.

In the particular example of FIG. 4, a microprocessor 100 performs the functions of monitoring the various inputs from the sensors 101, turning on any of the failure indicators if the corresponding sensor fails to detect a seed during a specified period of time, turning on the positive-operation indicator if seeds are detected in all rows, turning on the alarm for a period of time in the event of one or more row failures, and providing a visual indication, for example by flashing the failure indicator, of the row with the first failure. The planter monitor system may have a user-adjustable time period for determining failure in a row and is illustrated by switch 105. The flashing function is useful for monitoring purposes since it allows the operator to stop the planter without having to memorize which row sensed the failure and then be able to look at the console after all planting operation has ceased (in which case all failure indicators will be energized) and will determing the row that caused the original failure. This feature is particularly useful for planter monitors with a large number of rows such as, for example, in wheat planting machines.

The failure indicators may be any type of visual device such as lamps or light emitting diodes (LED's) and are designated 129 through 136; if they are the latter, with each LED is associated a resistor (120 through 127) to limit the current in the LED. In a similar manner, the proper-operation indicator may be a lamp or LED 137 and may have an associated resistor 128. The alarm 104 may be any audible device such as a piezoelectric buzzer. In the event that the current-drain requirements of the indicators and alarm are in excess of the output capability of the microprocessor, with each of these outputs will be associated a driver circuit (110 through 119).

For normal operation, virtually all microprocessors require a crystal 106 for timing purposes and a power-on reset circuit, shown as 107 and 108, to insure proper start-up of the internal program when power is first turned on. It is assumed in FIG. 4 that the particular microprocessor is one of the single-chip variety and contains the central processing unit (CPU), random access memory (RAM), internal timers, input/output (I/O) ports, and operating program stored in some form of read-only memory (ROM). An example of such a single-chip microprocessor is the Intel 8048 or the Motorola 6805. If the capabilities of the microprocessor are not sufficient to handle the required number of sensors and indicators, additional microprocessor peripheral chips are required.

Additional monitoring functions, such as seed counting, comparing seed counts of the rows to determine if any rows have counts that are substantially different from the remaining rows, and determining seed populations, may be performed by the microprocessor 100. Furthermore, other monitoring functions which might require additional sensors, such as bin level sensing, temperature sensing, air pressure sensing, and planter speed sensing (which would be useful to determine seed populations on a per-acre basis) could also be performed by the microprocessor 100. Thus the monitor system could be readily expanded in function simply by adding appropriate sensors and output indicators, each being interfaced to input or output ports of the microprocessor 100.

Figure 5:
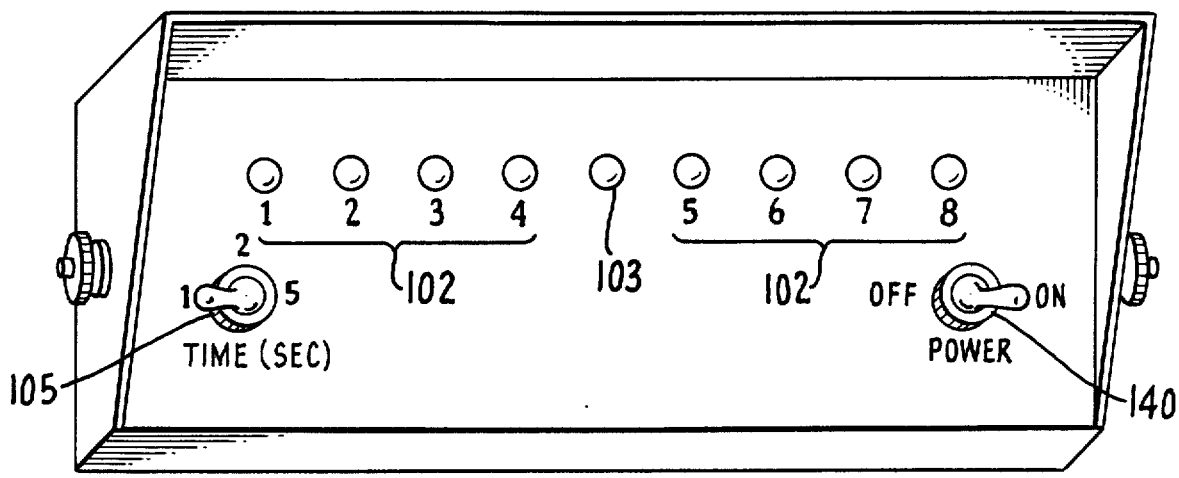
FIG. 5 is an elevational view of the front panel of the console for an eight-row planter monitor system.

FIG. 5 shows a front view of the console for an eight-row planter monitor system as described above. The front panel includes the time period select switch 105, a power on-off switch 140, eight red LED failure indicators 102 (one for each row being monitored), and a single green LED proper-operation indicator 103. The top of the console extends forward beyond the surface of the front panel to form a sun shield and thereby improve readability for operation in bright sunlight.

FIG. 6 illustrates the sensor electronics and detector circuit for a second form of the invention using a circuit technique whereby a plurality of sensors may be monitored by a single set of electronics by means of time multiplexing. The detector consists of an oscillator 150, a plurality of drivers 151, a multiplexer 154, an amplifier 155, an integrator 156, a differentiator 157, a comparator 158, and a microprocessor 159. The drivers 151 are each connected to an array of sensors 153 which have corresponding receiver buffer circuits 152. The outputs of the buffers are connected to the multiplexer 154. The array of sensors is in the form of a matrix whereby the drivers 151 are connected to the rows of the matrix and the multiplexer 154 is connected to the columns of the array. By using a matrix pattern for the array, a group of R drivers and C multiplexers can monitor an array of R times C sensors thereby minimizing either the number of electrical components required or minimizing the cost of the circuitry. In the particular example, two drivers (R=2) and four multiplexers (C=4) can monitor eight (R×C=2×4) individual sensors. The transmitter circuit consists of an oscillator 150 and drivers 151. The oscillator 150 is formed by two logic gates 165 and 168, resistors 166 and 169, capacitor 167, and crystal 170 and generates a signal of constant frequency which is applied to one input of all drivers 151. The drivers are each composed of a logic gate buffer 171 or 177, two resistors 173 and 174 or 179 and 180, a capacitor 172 or 178, a transistor 175 or 181 and a transformer 176 or 182. The second input of each driver at 171 and 177 is connected to an output port of the microprocessor 159. By selectively using the driver control lines 238, the microprocessor can enable one driver at a time. Thus only one row of the array of sensors will be driven at a time. The output of the enabled driver will be at the transformer secondary 176 or 182 and will be a sinusoidal signal of frequency equal to that of the crystal 170 and of sufficient amplitude to perform seed detection in the sensors.

Each of the sensors 183 through 190 have an associated receiver or buffer circuit which is this particular example is a pair of diodes 191 through 206. Although one could utilize more-complex buffer circuits at each sensor, the use of a pair of diodes provides a number of advantages. First, diodes are probably the simplest and least expensive of the many possible combinations. Second, the outputs of all sensors in a column can be wire-ored; that is, the outputs may be connected together without adverse effects. Third, the diodes perform a rectification operation which desensitizes the interconnection wires to the effects of stray capacitance and electrical interference.

The physical shape of the sensors 183 through 190 can be virtually identical to that described in FIG. 1 or FIG. 2 or any other similar arrangement. The primary difference between the sensors in this form of the invention and the form of the invention discussed previously is that in this form the receiver circuits at each sensor are greatly simplified and the size of the box at each sensor can be significantly reduced.

The outputs of the receiver circuits are half-wave rectified currents due to the operation of the diodes 191–206. The current in any one column will be that of the sensor appearing at the intersection of the column and the particular row whose driver is energized. The multiplexer 154, comprised of FET switch pairs 207 and 208 through 213 and 214 and inverters 215 through 218, is connected to a output port of the microprocessor 159 through multiplexer control lines 239. In normal operation, only one of the multiplexer sections is enabled at one time and the rectified current from the sensors in the disabled columns is steered to ground by FET's 207, 209, 211 or 213. Only the selected current from a particular column will be fed to amplifier 155. By a proper scanning process, amplifier 155 can be sequentially affected by each sensor. The output of amplifier 155, which consists of op amp 219 and resistor 220, is dependent on the rectified current in the selected sensor which in turn is dependent on the dielectric constant of the region between the electrodes of the selected sensor. Very little shunting of the electric fields inside the sensor occur and, as a consequence, relatively large changes in current fed to amplifier 155 occur as a result of the passage of only a single seed between the electrode means of the selected sensor.

Integrator 156, which is comprised of resistors 221, 222 and 223, capacitors 224 and 225 and op amp 227, acts as a dc restoring circuit by injecting a current through resistor 226 back to amplifier 155 so as to keep the output voltage of amplifier 155 at a nominal value depending on the values of resistors 221 and 222. The inclusion of the integrator 156 extends the range of the detector circuit and allows each sensor to operate over a wide variation in capacitance between the sensor electrode means. Furthermore, integrator 156 allows the sensors to operate even if the space between the electrodes is virtually packed with dust, a condition which might otherwise cause amplifier 155 to saturate.

Differentiator 157, comprised of capacitor 228 and resistor 229, generates an input to comparator 158 which is dependent on the time rate of change of the capacitance between the selected sensor's electrodes means. That in turn is dependent on the passage of seeds between those electrode means. Comparator 158 compares the output of the differentiator 157 to a fixed value determined by the setting of potentiometer 230, and produces an output equal to a logical ONE whenever a seed passes between the electrode means of the selected sensor.

The microprocessor 159 receives the output of the comparator 158 and after a short delay to allow the various signals to settle determines whether seeds are being sensed by a particular sensor. As soon as the microprocessor determines that a seed has been sensed, it can proceed to the next sensor in the sequence. Alternatively, the microprocessor can count the number of seeds during a given period of time and determine if the seed flow rate is either within prescribed limits or within a tolerance band relative to the seed flow rates in all the other sensors. Depending on the particular program in the microprocessor, a variety of test conditions can be performed in order to determine whether a particular row had "failed." The simplest criterion for failure of a planting row might be that no seeds be detected during a specified period of time. In this case, the value of the time period could be user-programmable as illustrated by switch 231. Thus, the microprocessor performs three main functions. First it causes the array of sensors to be scanned in a predetermined pattern. Second, it decides, based on a specific set of criteria, whether each row of the planter is planting properly. Third, the microprocessor provides output signals to the console for control of the various indicators and alarms, shown in the figure as 235 through 237. Outputs 235 through 237 are shown as being in a serial data format in order to simplify the cabling requirements of the monitor system.

Additional monitoring functions, such as seed counting, comparing seed counts of the rows to determine if any rows are substantially different from the other rows, and determining seed populations, may be performed by the microprocessor 159. Furthermore, other monitoring functions which might require additional sensors, such as bin level sensing, temperature sensing, air pressure sensing, and planter speed sensing (which would be useful to determine seed populations on a pre-acre basis) could also be performed by the microprocessor 159. Thus, the monitor system could be readily expanded in function simply by adding appropriate sensors, each being interfaced to an input port of the microprocessor 159.

The detector circuit described above is not limited to using only one combination of amplifier 155 through comparator 158 circuits. Two such sections could be employed, each connected to half of the columns of the sensor array. The result of such a change to the detector circuit would be to increase the complexity and cost of the total circuit by less than a factor of two while at the same time increasing the speed of the scanning process by a full factor of two since two comparator outputs would be generated simultaneously. This process of increasing the speed of the system at the expense of increasing the circuit complexity and cost could be continued until the complexity approaches that of the previous form of the invention. Thus, there is a whole class of possible planter monitor systems whose circuit complexity can be traded against circuit speed. That is, if the planter monitor system is allowed to look at each sensor for a period of time and is further allowed to not look at that same sensor until all other sensors have been looked at, then the second form of the invention is the most cost effective monitor. Alternatively, if all sensors must be monitored on a continuous basis, then the first form of the invention is necessary. Combinations that are between the two extremes are possible by using the second form of the invention with an increased number of amplifier 155 to comparator 158 sections.

Figure 7:
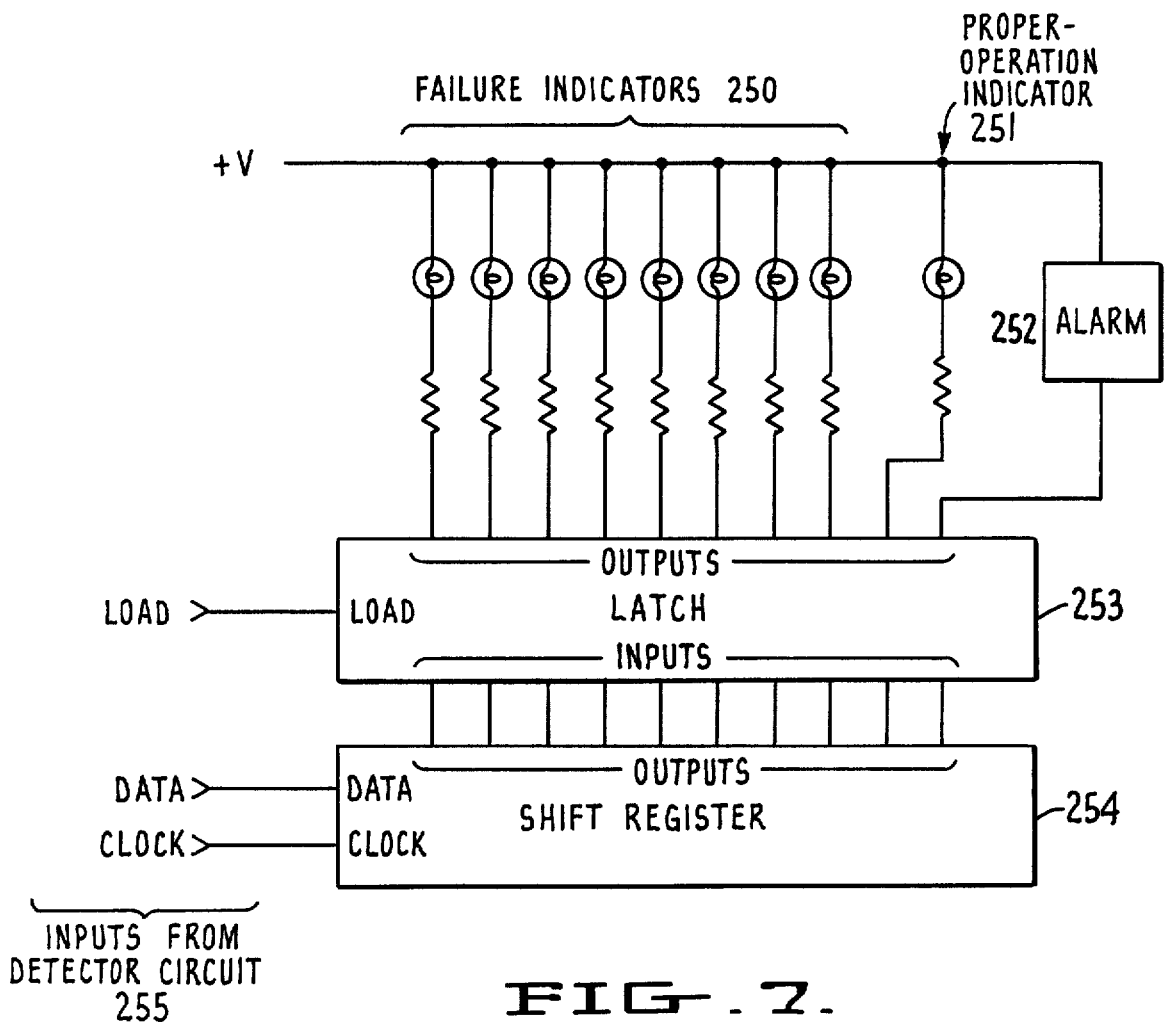
FIG. 7 is an electrical schematic diagram of the console electronics for an eight-row planter monitor system to be used with the circuits of FIG. 6.

FIG. 7 is an electronic schematic diagram for an eight-row monitor system console which is compatible with the circuit of FIG. 6. The console is comprised of row failure indicators 250, a proper-operation indicator 251, an alarm 252, a latch circuit 253 and a shift register circuit 254. The shift register 254 receives signals 255 from the detector circuit which indicate the status of the planting machine. As illustrated, the signals are in a serial data format which allows the cabling from the detector circuit to the console to be simplified. The shift register 254 converts the serial data to parallel format which is then latched by the latch circuit 253 in response to the load signal from the detector circuit. The failure indicators may be any type of visual device such as lamps or light emitting diodes (LED's); if the latter, resistors would be included with the LED's to limit their current, as shown. In a similar manner, the proper-operation indicator 251 may be a lamp or LED and may have an associated resistor for current limiting. The alarm 252 may be any audible device such as a piezoelectric buzzer. If the output drive capability of the latch 253 is not sufficient to drive all of the indicators, buffers (not shown) would have to be placed between the latch outputs and the indicators.

One property of the console electronics for the second form of the invention, as shown in FIG. 7, is that the circuitry is relatively simple. Thus, the console electronics could be packaged in a relatively small box and might take the form of a small instrument on the dashboard of the tractor or other vehicle pulling the planter.

The passage of electrically conductive particles along their path of travel between the transmitter and receiver electrode means can also be sensed or monitored by the described circuitry. Such particles, as they pass, vary the equivalent gap between the electrode means.

Various modifications to the described embodiments may be apparent to those familiar in this art within the scope of the invention which is defined in the following claims. For example, a d-c potential, rather than the described a-c, may be applied across the sensor electrode means with appropriate changes in transmitter and receiver circuit means to monitor changes in capacitance as particles pass between the electrode means. In an a-c system, the change in oscillator frequency rather than capacitance may be sensed by appropriate receiver circuits or the system could use a single electrode and ground as the other.

I claim:

1. A system for monitoring small discrete particles having a high dielectric constant, such as seeds, that pass along a path, comprising
   a sensor having at least one transmitter and one receiver electrode means spaced from one another and electrically exposed to said path passing between them;
   transmitter circuit means applying to said transmitter electrode means a constant electrical signal to produce an electrical sensing field between said electrode means transverse to said path;
   receiver circuit means detecting a change in electrical energy received by said receiver electrode means from said transmitter electrode means in response to a particle passing on said path in proximity to said electrode means; and
   a grounded conductive shield extending further along said path than the electrode means sufficiently for both isolating said electrode means from the external environment and for confining said transverse electric sensing field to a short length of said path between electrodes.

2. The system of claim 1 wherein said electrical signal is a constant frequency alternating electrical signal.

3. The system of claim 1 further comprising electrical insulating layers overlying each of said electrode means.

4. The system of claim 2 wherein the receiver circuit means includes a rectifier having an output that is responsive to the dielectric constant of that portion of the particle path between the electrode means.

5. The system of claim 4 further including in the receiver circuit means an operational amplifier converting the rectifier output to a voltage and an integrator providing a d-c restoring current back to the amplifier for extension of the dynamic range of the receiver circuit means.

6. The system of claim 4 further comprising in the receiver circuit means a differentiator to convert the rectifier output to a signal dependent upon the time rate of change of impedance between said electrode means and a comparator for that converted signal and a selectable reference value to produce a digital output when said converted signal exceeds the reference value.

7. The system of claim 6 further comprising microprocessor means responsive to the digital output of said receiver circuit means to manipulate means on said console indicative of the state of said digital output.

8. A system for monitoring small particles having a high dielectric constant, such as seeds, that pass along a plurality of separate paths, comprising
   a plurality of sensors, one for each path and arranged in a matrix having rows and columns, each sensor having at least one transmitter and one receiver electrode means spaced from one another and electrically exposed to said path passing between them;
   transmitter circuit means including a source of constant electrical signal to produce an electric sensing field between said electrode means transverse to said path;

a grounded conductive shield extending further along said path than the electrode means sufficiently for both isolating said electrode means from the external environment and for confining said transverse electric sensing field to a short length of said path between electrodes;

a separate driver for selectively connecting said source to the transmitter electrode means for one row of sensors;

separate receiver circuit means connected to the receiver electrode for each sensor;

a multiplexer interconnecting the output of the separate receiver circuit means for the sensors in each column of said matrix; and microprocessor means gating in sequence the drivers for the rows of sensors and simultaneously enabling the multiplexer to scan the receiver circuit output for the sensors in the gated row.

9. The system of claim 8 further including a shift register for serial receipt of signals from said microprocessor indicative of the status of each sensor; and a latch circuit for receiving the shift register output to simultaneously manipulate means on said console indicative of the status of each sensor.

10. A system for monitoring small electrically conductive discrete particles, such as the size of seeds, that pass along a path, comprising a sensor having at least one transmitter and one receiver electrode means spaced from one another and electrically exposed to said path passing between them;

a grounded conductive shield extending further along said path than the electrode means sufficiently for both isolating said electrode means from the external environment and for confining the transverse electric sensing field between said electrode means to a short length of said path between electrodes;

transmitter circuit means applying to said transmitter electrode means a constant electrical signal to produce said electric sensing field transverse to said path; and receiver circuit means detecting a change in electrical energy received by said receiver electrode means from said transmitter electrode means in response to a particle passing on said path in proximity to said electrode means.

11. The system of claim 10 wherein said electrical signal is a constant frequency alternating electrical signal.

12. The system of claim 11 wherein the receiver circuit means includes a rectifier having an output that is responsive to the dielectric constant of that portion of the particle path between the electrode means.

* * * * *

UNITED STATES PATENT OFFICE
CERTIFICATE OF CORRECTION

Patent No. 4,710,757   Dated December 1, 1987

Inventor(s)   Wayne C. Haase

It is certified that error appears in the above-identified patent and that said Letters Patent are hereby corrected as shown below:

col. 1, line  4; "transverse" should be -- traverse --;
   col. 1, line 25; "what as" should be deleted;

col. 2, line 33; "for receiving electrical" should be deleted and -- , receiver electrode means electrically -- substituted therefor;
   col. 6, line 21; "oscilator" should be -- oscillator --;
   col. 7, line 16; after "rate" should be added -- of change of --;

col. 9, line 27; "is" should be -- in --;

col.10, line 66; "pre-acre" should be -- per-acre --.

Signed and Sealed this

Fourteenth Day of June, 1988

*Attest:*

DONALD J. QUIGG

*Attesting Officer*   *Commissioner of Patents and Trademarks*